United States Patent [19]

Jourdan-Laforte et al.

[11] Patent Number: 4,587,264
[45] Date of Patent: May 6, 1986

[54] DISINFECTION AND STERILIZING SOLUTION OF PERACETIC ACID AND NITRIC ACID

[75] Inventors: Eric Jourdan-Laforte, Paris; Daniel Le Rouzic, Aubervilliers, both of France

[73] Assignee: L'Air Liquide, Societe Anonyme pour l'Etude et l'Exploitation des Procedes Georges Claude, Paris, France

[21] Appl. No.: 463,617

[22] Filed: Feb. 3, 1983

[30] Foreign Application Priority Data

Feb. 24, 1982 [FR] France .............................. 82 03000

[51] Int. Cl.$^4$ ............................................ A61K 31/20
[52] U.S. Cl. .................................................. 514/557
[58] Field of Search .......................... 424/317; 514/557

[56] References Cited

U.S. PATENT DOCUMENTS 4,051,058 9/1977 Böwing et al. .
4,051,059 9/1977 Böwing et al. .
4,297,298 10/1981 Crommelynck .

FOREIGN PATENT DOCUMENTS 0024219 2/1981 European Pat. Off. .
2321302 3/1977 France .
55-133062 9/1980 Japan .................................. 424/317
2087724A 9/1981 United Kingdom .

OTHER PUBLICATIONS

Gregory, "Uses and Applications of Chemicals and Related Materials", pp. 408–410.
Lück et al, "Influence of Acidic Detergents on the Reduction of the Surface Count of Stainless Steel Pipes", S. Afr. J. Dairy Technol, 1981, 13(4):87–92.

Primary Examiner—Stanley J. Friedman
Attorney, Agent, or Firm—Browdy and Neimark

[57] ABSTRACT

Commercial solutions of noncorrosive and time-stable carboxylic peracids, particularly peracetic acid, contain an acid of oxidizing nature, such as nitric acid, present in a weight percentage at least equal to that of the carboxylic peracid. Such solutions, diluted with ordinary water, are useful for the sterilization and microbiological disinfection of aseptic enclosures, and of equipment of the food industry, particularly the milk industry, with reduced risk of corrosion to the equipment.

11 Claims, 3 Drawing Figures

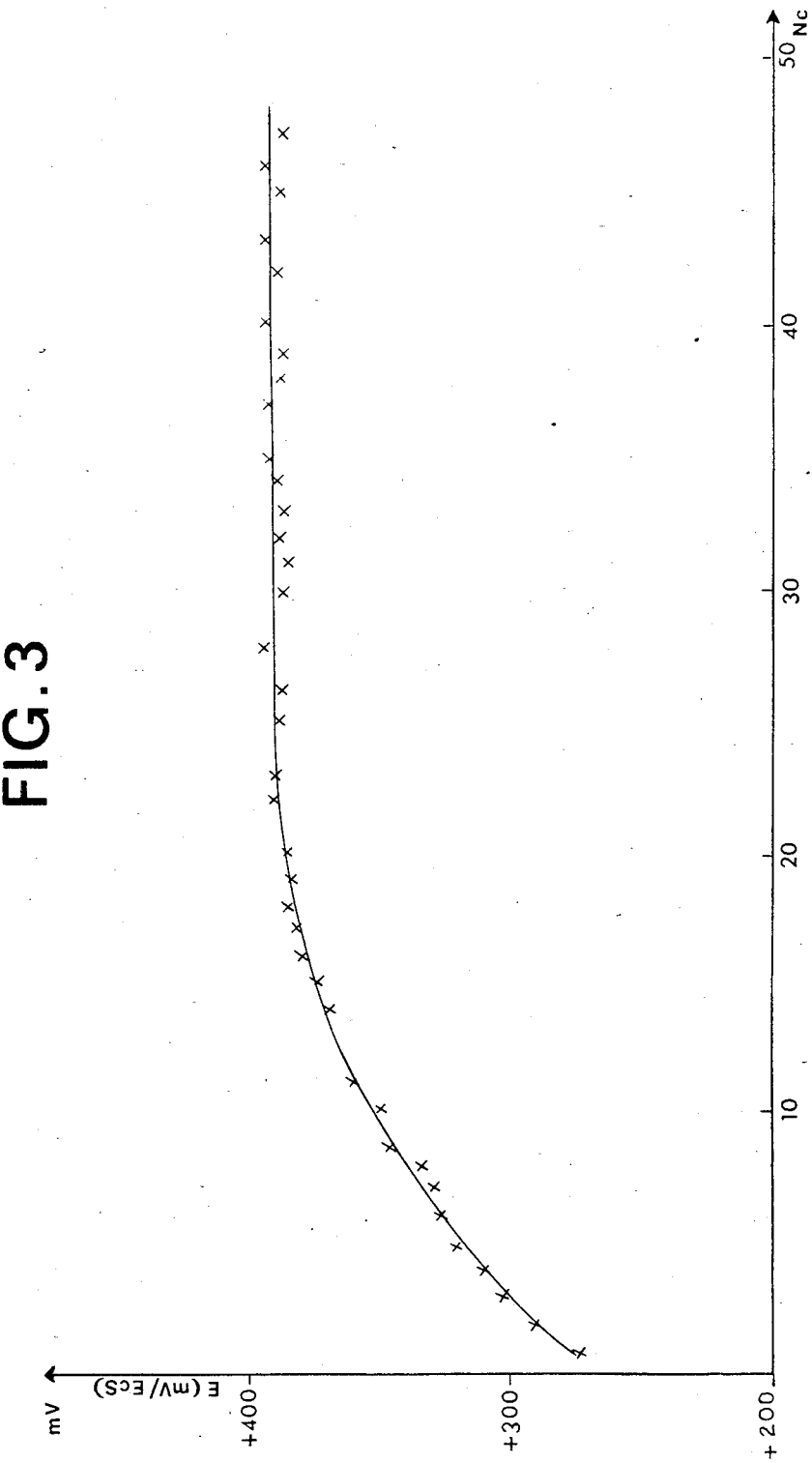

DISINFECTION AND STERILIZING SOLUTION OF PERACETIC ACID AND NITRIC ACID

FIELD OF INVENTION

This invention relates to commercial solutions of non-corrosive and time-stable carboxylic peracids.

BACKGROUND

Solutions of carboxylic peracids are generally obtained by the action of hydrogen peroxide on the corresponding carboxylic acid. French Pat. No. 2,462,425, discloses a process especially applicable to the preparation of stable dilute solutions of peracetic acid in which, in a first stage, a concentrated solution of aliphatic carboxylic peracid is prepared from the acid or the corresponding anhydride and concentrated hydrogen peroxide, in the presence of the minimum amount of a strong acid catalyst necessary to obtain balance of the system in a maximum period of 48 hours; and, in a second stage the concentrated solution of aliphatic peracid is diluted with a solution that contains at least a reactive constituent to bring the concentration of aliphatic peracid to the nominal concentration of the mixture.

This process makes it possible to prepare rapidly, on an industrial scale, solutions of aliphatic carboxylic peracids in aqueous form that contain several percents by weight of a peracid and that remain stable over time. Thus, dilute solutions containing between 1 and 20% by weight of carboxylic peracid, particularly monoperacetic acid, are easily obtained in very good industrial conditions. Preferably, the concentration of the prepared solutions is from 2 to 5% by weight of carboxylic peracid.

These dilute solutions of peracids are more appreciated because they are easier to transport and handle than concentrated solutions, because of the combustive nature of the peracid, and sometimes because of its odor and its irritating properties with respect to the skin, eyes and respiratory tract.

Solutions of peracetic acid, for example, are particularly suited for the sterilization of aseptic enclosures, such as incubators for premature animals or the growing of axenic animals, and the disinfection of hospital rooms and equipment. These solutions are also used to disinfect surfaces of work areas, rooms and equipment of the food industry. There are also applications such as disinfection and sterilization in operations for cleaning the inner walls of apparatus and circuits of manufacturing units of the food industry.

As far as food technology is concerned, stainless steel tends to be necessary more and more to the detriment of aluminum and other traditional materials (galvanized iron, wood, etc.). The composition of the most widely used stainless steel contains 18% chromium and 10% nickel. Although this stainless steel is virtually inert with respect to food products, most of the disinfecting and sterilizing agents authorized in the food industry cause corroding of the stainless steel; that is the case, for example, with chlorinated products.

Generally, commercial solutions of peracetic acid are diluted before use with water to bring the concentration of peracetic acid to between 30 and 300 mg/liter. No matter what its concentration, a solution of peracetic acid, diluted with deionized water, does not corrode the stainless steels currently used in the food industry, but taking into account the volumes of water called into play, particularly in disinfection in the food industry, the disinfecting of equipment by this process using deionized water is economically prohibitive.

When the water for dilution is ordinary water which contains traces of dissolved chlorides, a cavernous or pitted corrosion of certain grades of stainless steel is found. This corrosion is connected to the presence of chlorides in ordinary water which are oxidized by the peracids. This corrosion is particularly insidious because it occurs in places where the liquids are preferably not stirred; it is located, for example, in the dead zone of joints, connections valves and pipes. These dead zones are difficult to clean during rinsing operations with clear water, followed by cleaning with soda and nitric acid, which usually precede the disinfection phase.

This problem is particularly critical for the milk industry. Actually, milk has a marked tendency to leave on the inner walls of the pipes and apparatus, especially when they are heated, a film of organic matter consisting of fatty matter, nitrogenous matter and inorganic salts; this contamination promotes the growth of microbial flora. This problem is obviously increased further when there is a phenomena of cavernous corrosion which makes bacterial sites almost inaccessible to the cleaning and disinfecting agents.

On the other hand, because milk is an environment favorable to the growth of germs, the officials of the milk industry are particularly concerned with keeping their equipment in a satisfactory state of asepsis; consequently, they must look for the best compromise between the effectiveness of the cleaning and disinfecting agents and the risk of damage to their equipment. Under these conditions, the use of an effective disinfecting agent on the microbiological level which is moreover noncorrosive with respect to the equipment, is particularly valued.

SUMMARY

It has now been found that the addition of an acid of an oxidizing nature to a commercial solution of carboxylic peracid considerably reduces the risk of corrosion of the stainless steel when the commercial solution of peracid is diluted with ordinary water containing chlorides. The acid of an oxidizing nature, introduced in a suitable amount, makes it possible to reduce the risks of corrosion because the oxidation potentials, i.e. the starting points for the corrosion, are clearly higher than those encountered under usual conditions for disinfecting stainless steel equipment using peracetic acid without nitric acid or the like.

BRIEF DESCRIPTION OF DRAWING

FIG. 3 is a graph showing the movement of free potential (E1) 18-10 stainless steel as a function of the number of use and cleaning cycles, simulating the effect of a solution of the invention on stainless steel circuits in the milk industry.

DETAILED DESCRIPTION OF EMBODIMENTS

Figure 1:
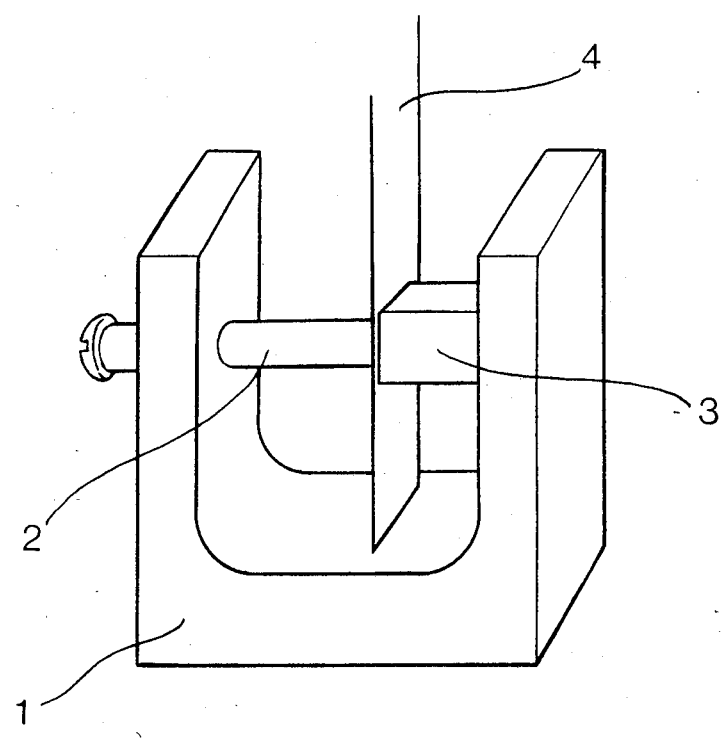
FIG. 1 is a schmatic perspective view.

Nitric acid leads to very valued results, by making it possible mainly to eliminate the problem of cavernous corrosion observed especially curing the disinfecting of the equipment of the food industry made with the current grades of stainless steel, and when the commercial solutions of carboxylic peracetic acid, are diluted with ordinary water. Moreover, nitric acid incorporated in the commercial solution of peracetic acid is an inexpensive anticorrosive agent, authorized for food disinfecting and which does not adversely affect the stability of the peracetic acid. Actually, despite a strong concentration of nitric acid present in the commercial solutions of peracid, it remains very stable and can be kept several months.

Advantageously, the acid of an oxidizing nature, such as nitric acid, is present in the commercial solutions in a weight percentage at least equal to that of the carboxylic peracid, preferably 3 to 5 times the weight percentage of the organic peracid in the commercial solution. The diluted commercial solutions containing between 1 and 20%, preferably 2 to 5% by weight of carboxylic peracid, contain an amount of nitric acid such that the concentration of nitric acid will be preferably between 6 and 15% by weight. In particular, solutions at 2% by weight of peracetic acid and 8% by weight of nitric acid, diluted with water to provide 50 mg of peracidic acid per liter, do not cause cavernous corrosion of type 18-10 stainless steel.

The commercial solutions of carboxylic peracids according to the invention find applications as disinfecting and sterilizing agents of aseptic enclosures and in the apparatus and circuits of the food industry, particularly in the field of the microbiological disinfecting of installations in the milk industry.

These solutions of carboxylic peracids used for disinfecting and sterilizing are obtained by introduction, in the commercial solution of carboxylic peracid, containing in particular 2 to 5% by weight of peracetic acid, nitric acid in such an amount that its weight percentage corresponds to 3 to 5 times that of the peracetic acid; then dilution with ordinary water to a concentration of peracetic acid between 30 and 300 mg/liter.

After rinsing, cleaning with soda under standard conditions, rinsing again with running water, the apparatus and circuits particularly of the milk industry are microbiologically disinfected by simple treatment with dilute solutions with a concentration between 30 and 300 mg/liter of peracetic acid and that contain nitric acid, for a relatively short contact time on the order of 10 to 30 minutes, preferably 15 to 20 minutes, at ambient temperature.

Examples which illustrate the invention in a nonlimiting way are given below.

The runs are made with austenitic stainless steel with the following composition (mass %): chromium=18; nickel=9.9; carbon=0.025; maganese=1.5. Samples are cut in a 100×50×2 mm size, from cold rolled industrial sheets hypertempered at 1050° to 1150° C. The faces of the samples—which in fact constitute the test surface—are polished under a current of water with sand paper (No. 220-80 micrometers), then passivated in the air for 30 minutes. The test surface is delimited by masking with varnish, such as the varnish sold under the trademark "Lacomit N 256A," to prevent any undesirable corrosion at the waterline. The test surface is about 50 cm² counting the two faces of the test piece.

An experimental device, shown in FIG. 1, is used to artificially create a small surface on the order of 0.5 cm² in which a cavernous corrosion preferably will develop. This device is composed of a plastic stirrup piece 1 equipped with a screw 2 of the same material, on one of its branches, and with a rubber stop 3 on the other branch. This rubber joint or stop 3 is attached by simple screwing of the screw 2 on the previously prepared test piece 4.

Figure 2:
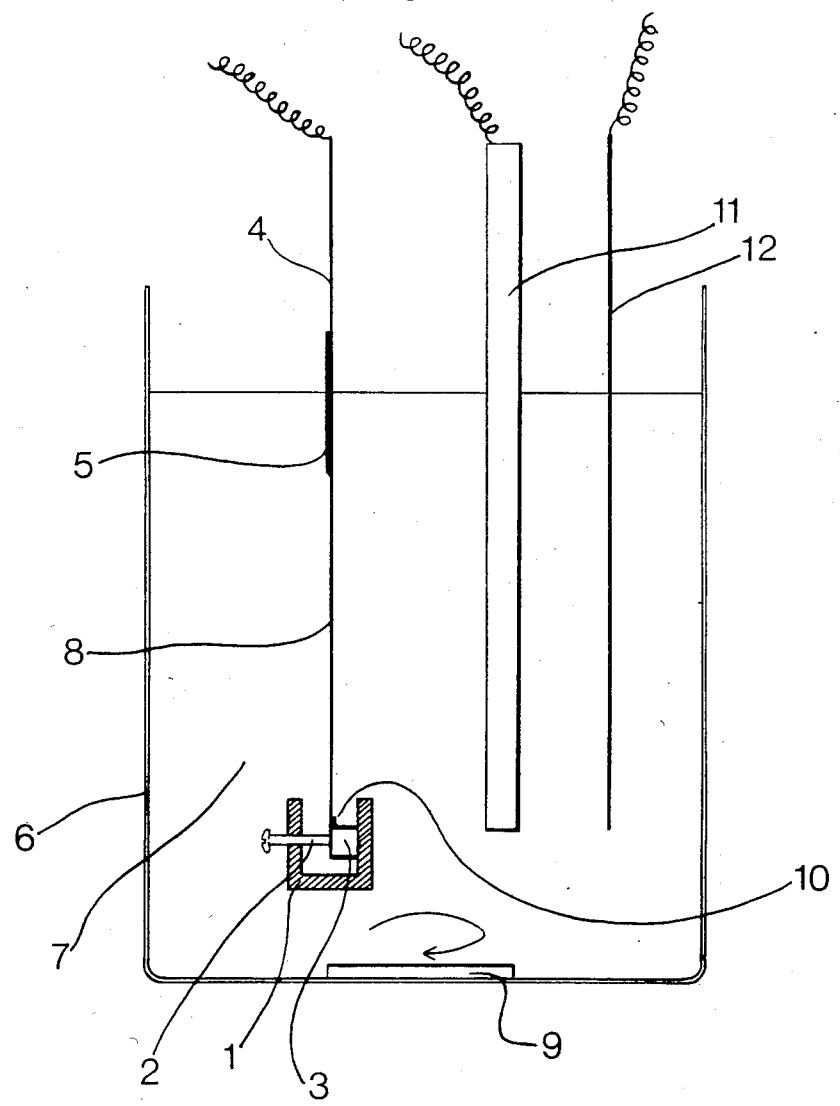
FIG. 2 is a vertical sectional view of testing equipment used to evaluate solutions of the present invention in comparison with other solutions.

Then the cavernous corrosion in the experimental device shown in FIG. 2 is studied. The test piece 4 covered with the insulating varnish 5 at the air-water line and equipped with the stirrup unit according to FIG. 1, is immersed in the tank 6 containing the solution 7 to be studied, at such a depth that all the unvarnished test surface 8 is immersed. The solution is stirred by action of the bar magnet 9. The cavernous corrosion occurs in area 10. Between the test piece and a saturated calomel electrode (SCE) 11, serving as a reference, a millivolt-meter with strong input impedance ($10^6$ megohms)—not shown—measures the difference in potential. When no cavernous corrosion has been able to be detected after 24 hours, the unit is supplemented with a platinum electrode 12, making possible the recording of the variations of intensity when they are imposed, by a potentiostat—not shown—as increasing potential difference between the first two electrodes.

A series of runs are conducted to compare peracetic acid and sodium hypochlorite. There are used, first, a solution of commercial sodium hypochlorite titrating 35.6° chlorometric; second, a solution of peracetic acid without nitric acid; third, a solution of peracetic acid with 6.8% nitric acid; and fourth, a solution of peracetic acid with 8% nitric acid having the following composition:

| Peracetic acid | 2 | % by weight |
|---|---|---|
| Acetic acid | 6.1 | " |
| Hydrogen peroxide | 19.9 | " |
| Nitric acid | 8.0 | " |
| Hydroxyethane-diphosphonic acid | 0.3 | " |
| Water | 63.7 | " |

The test solutions are prepared by dissolving the afore-referenced concentrated products in ordinary water the content of which in equivalent NaCl is about 50 mg/l.

The study of the corrosion is performed by using electrochemical methods which consist in tracing the curves of the electrochemical potential of the stainless steel as a function of time (curve E as a function of time). All the values of potential are expressed in millivolts with respect to the saturated calomel electrode (mV/S.C.E.). When the cavernous corrosion spontaneously develops, which is reflected by a slight but sudden drop of potential, one measures the time before cavernous corrosion ($t_{cav}$) and the value of the corrosion potential ($E_{cav}$), $t_{cav}$ still being the essential criteria of resistance to the cavernous corrosion.

When no corrosion is produced at the end of curve E as f (t), then the value of the free potential (E1) of the stainless steel after 24 hours is measured (E1-24th.) then from this value the curve of anodic polarization is plotted, i as f (E), by making the potential E vary from 1 to 6 mV/h. When the cavernous corrosion develops, the intensity increases; the potential at which this increase occurs is called cavernous corrosion potential ($E_{cav}$). In this case, the difference $E_{cav}$−E1-24h. is considered as representative of the resistance to cavernous corrosion.

Two types of runs are made. According to the first type ("prolonged immersion"), the samples of stainless steel, after polishing and passivation in air for 30 minutes, are immersed either in (1) a sodium hypochlorite solution having 300 mg of $Cl_2/l$, at 20° C., or in (2) a solution of peracetic acid of 50 mg/l of peractic acid, or in (3) a solution of peracetic acid of 50 mg/l additionally containing nitric acid at 20° C., for periods that could reach 24 hours when no spontaneous corrosion occurs.

varies from 115 to 145 mV, which shows that the risk of cavernous corrosion is almost absent, even for periods of immersion greater than 24 hours, with a 2% by weight peracetic acid solution that contains 8% by weight of nitric acid.

TABLE 1

Influence of the nature of the disinfectant product on the period before cavernous corrosion ($t_{cav}$), the value of the cavernous corrosion potential ($E_{cav}$), the value of the free potential ($E_1$-24th) and the margin of safety for use (difference between $E_{cav}$ and $E_1$-24th) of the stainless steel of the 18-10 type; 220 polishing; passivation in air for 30 minutes; testing temperature 20° C.

| PRODUCT | Concentration of active substance mg/l | Curve E = f (t) | | $E_1$-24th mV/SCE | Curve i = f (E) | | |
|---|---|---|---|---|---|---|---|
| | | E cav mV/SCE | t cav | | Polarization speed mV/minute | E cav mV/SCE | E cav-E1-24th mV/SCE |
| Sodium hypochlorite | 300 | +95 | 7 h | | | | |
| solution at 36° | 300 | +25 | 13 h 40 | | | | |
| chlorometric | 300 | +135 | 6 h 30 | | | | |
| 2% peracetic acid | 50 | +340 | 4 h 10 | | | | |
| solution | 50 | +300 | 2 h 05 | | | | |
| | 50 | +355 | 4 h 26 | | | | |
| | 50 | +328 | 4 h 33 | | | | |
| 2% peracetic acid solution with 6.8% $HNO_3$ | 50 | +420 | 22 h | | | | |
| 2% peracetic acid solution with 8% $HNO_3$ | 50 | | | +435 | 1 | +580 | 145 |
| | 50 | | | +475 | 6 | +600 | 125 |
| | 50 | | | +465 | 2 | +580 | 115 |

The second type of test ("alternating/immersion-emergence") has as its object to simulate the industrial practice where the material is successively in contact with various mediums, for example milk, cleaning and disinfecting solutions, waters for rinsing and following its corrosion behavior; it can possibly be different from that of samples which are only in contact with the disinfectant solution. Consequently, some stainless steel samples are subjected to the following operations: immersion in milk at 70° C. for 10 minutes; rinsing in running water for 5 minutes; cleaning in a 2% soda solution at 70° C. for 10 minutes; rinsing in running water for 5 minutes; disinfection in a 50 mg/l peracetic acid solution at 20° C. for 15 minutes and rinsing in running water for 5 minutes. All of these operations together constitute 1 cycle. During the disinfecting operation, the movement of the potential of the stainless steel is recorded and its value, at the end of each disinfection, is noted.

The results obtained according to the first type of test by prolonged immersion are set forth in table 1.

The results of this table show that the solution of sodium hypochlorite with 300 mg of $Cl_2/l$ at 20° C. cause the cavernous corrosion of the stainless steel after periods of contact varying from 6 hours, 30 minutes to 13 hours, 40 minutes. Peracetic acid without oxidizing acid (e.g. nitric acid) caused cavernous corrosion in roughly 2 to 4¼ hours.

It is found that the solution of peracetic acid that initially contained 6.8% nitric acid causes cavernous corrosion after 22 hours. It should be noted that these periods are nevertheless largely greater than the disinfection period which is generally from 10 to 20 minutes. On the other hand, the solution of peracetic acid that initially contained 8% nitric acid gives no cavernous corrosion after 24 hours of testing.

Under the test conditions, the peracetic acid containing nitric acid is, therefore, much less aggressive than the sodium hypochlorite with regard to the stainless steel of the 18-10 type.

The margin of safety for use of the stainless steel E in contact with 50 mg/l peracetic acid solutions at 20° C., FIG. 3 of the accompanying drawing shown the movement of the free potential (E1) of the stainless steel of the 18–10 type as a function of the number of cycles in the test context with milk at 70° C. for 10 minutes; rinsing under running water for 5 minutes; followed by a cleaning with 2% soda for 10 minutes at 70° C.; then a rinsing under running water for 5 minutes; disinfection treatment with a commercial solution of 2% by weight peracetic acid containing 8% by weight of nitric acid used at an amount of 50 mg of peracetic acid per liter at 20° C., for 15 minutes; and a final rinsing with running water for 5 minutes.

The results are plotted on the curve, the y-axis showing the E potential (mV/SCE) expressed in millivolts mV and the x-axis the number of Nc cycles.

From reading the results that appear in FIG. 3, it is seen that the free potential E1 of the stainless steel, at the end of the various disinfections performed in the 50 mg/l peracetic acid solutions containing nitric acid varies from 275 to about/400 mV after 48 cycles. In practice, the free potential is stabilized from the 20th cycle. Now, the value of the cavernous corrosion potential, determined previously, is on the order of +580 mV (Table 1 curve i=f (E) column $E_{cav}$mV/SCE). Since the maximum value E1, at the end of 48 cycles levels off at about +400 mV, there is another margin of safety of 180 mV before there is actually a risk of cavernous corrosion. This shows that the commercial solution of 2% by weight peracetic acid containing 8% by weight of nitric acid, used in the amount of 50 mg peracetic acid per liter at 20° C., cannot cause the cavernous corrosion of the stainless steel of the 18-10 type.

It is to be understood that the invention is not limited to the embodiments disclosed which are illustratively offered and that modifications may be made without departing from the invention.

What is claimed is:

1. A concentrated solution for dilution with chloride ion-containing water to provide a diluted non-corrosive disinfecting and sterilizing solution, said concentrated solution containing between 1 and 20% by weight of peracetic acid, further containing nitric acid in a weight percentage 3 to 5 times that of said peracetic acid.

2. The concentrated solution according to claim 1, wherein said solution contains between 2 and 5% by weight of peracetic acid.

3. The concentrated solution according to claim 2, wherein the concentration of said nitric acid is approximately 8% by weight up to 5 times the weight percentage of said peracetic acid.

4. A diluted non-corrosive disinfecting and sterilizing solution comprising the solution according to claim 3 diluted with ordinary chloride ion-containing water to provide a concentration of peracetic acid therein of between 30 and 300 mg/liter.

5. The concentrated solution according to claim 1 wherein the concentration of nitric acid is approximately 6–15% by weight.

6. The concentrated solution of claim 1 comprising approximately 2% by weight of peracetic acid and 8% by weight of nitric acid.

7. A diluted, non-corrosive disinfecting and sterilizing solution comprising the solution according to claim 6 diluted with ordinary, chloride-containing water to provide a concentration of peracetic acid of about 50 mg of peracetic acid per liter.

8. The concentrated solution according to claim 1 containing, by weight, approximately 2% peracetic acid, 6.1% acetic acid, 19.9% hydrogen peroxide, 8% nitric acid, 0.3% hydroxyethane-diphosphonic acid and 63.7% water.

9. The concentrated solution according to claim 1 wherein the concentration of said nitric acid is approximately 8% by weight up to 5 times the weight percentage of said peracetic acid.

10. A method of preparing a disinfecting and sterilizing solution of a carboxylic peracid comprising introducing nitric acid into a 2–5% by weight commercial solution of peracetic acid, said nitric acid being added in such an amount that its weight percentage in the mixture corresponds to 3 to 5 times that of said peracetic acid; then mixing the resultant solution with ordinary water until a concentration of peracetic acid of between 30 and 300 mg/liter is obtained.

11. A method of disinfecting and sterilizing an aseptic enclosure or a food industry apparatus or circuit, comprising applying thereto the non-corrosive disinfecting and sterilizing solution according to claim 9.

* * * * *